(12) United States Patent
Peter

(10) Patent No.: US 6,314,789 B1
(45) Date of Patent: Nov. 13, 2001

(54) SENSOR UNIT FOR AIR QUALITY MEASUREMENT

(75) Inventor: Cornelius Peter, Buehl (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/486,202

(22) PCT Filed: Aug. 20, 1998

(86) PCT No.: PCT/DE98/02433

§ 371 Date: Aug. 4, 2000

§ 102(e) Date: Aug. 4, 2000

(87) PCT Pub. No.: WO99/10738

PCT Pub. Date: Mar. 4, 1999

(30) Foreign Application Priority Data

Aug. 23, 1997 (DE) ................................ 197 36 824

(51) Int. Cl.⁷ .............. G01N 19/10; F02D 4/00; H01C 7/00
(52) U.S. Cl. .............. 73/23.2; 123/686; 338/14
(58) Field of Search .................. 73/23.2, 23.31, 73/31.02, 31.05; 123/676, 684, 686, 687, 696, 697; 204/409, 424, 426, 427, 428; 338/14; 422/98

(56) References Cited

U.S. PATENT DOCUMENTS

| 4,151,503 | 4/1979 | Cermak et al. | 338/14 |
| 5,211,053 | 5/1993 | Nolting et al. | |
| 5,217,692 | 6/1993 | Rump et al. | 422/98 |

FOREIGN PATENT DOCUMENTS

| 0 527 258 | 2/1993 | (EP) . |
| 93 10441 | 5/1993 | (WO) . |

Primary Examiner—Hezron Williams
Assistant Examiner—Jay L. Politzer
(74) Attorney, Agent, or Firm—Kenyon & Kenyon

(57) ABSTRACT

A sensor unit is described, in particular an air quality sensor, having a first support element, on which are arranged a first sensor element and a first heat source, assigned to the latter, and having at least one further, second support element, on which are arranged a second sensor element and a second heat source, assigned to the latter. The two support elements are configured as a common support unit and, between them, have a heat barrier for thermal isolation.

11 Claims, 1 Drawing Sheet

SENSOR UNIT FOR AIR QUALITY MEASUREMENT

FIELD OF INVENTION

The present invention relates to a sensor unit, in particular an air quality sensor, having a first support element, on which are arranged a first sensor element and a first heat source, assigned to the latter, and having at least one further second support element, on which are arranged a second sensor element and a second heat source, assigned to the latter.

BACKGROUND INFORMATION

Sensor units of this type constitute so-called air quality dual sensors, which can carry out a carbon monoxide and a nitrogen oxide measurement for quantifying the exhaust gas quality of motor vehicle internal combustion engines. In modern internal combustion engines, a multiplicity of input parameters is processed in the course of electronic engine management. These are, for example, the instantaneous engine revolutions per unit time, the gas pedal position, etc. A further characteristic quantity for engine management is the pollutant concentration of the exhaust gases arising from combustion. These pollutants, as is conventional, are measured using sensors, the data from the sensors being taken into account in the engine management.

International Patent Application WO 93/10441, describes a conventional method which, for determining small quantities of carbon monoxide and nitrogen oxide in oxygen-containing gas mixtures, makes use of a sensor, whose electrical resistance changes in response to an increase in temperature. The magnitude of the change is a function of the carbon monoxide and nitrogen oxide concentration in the gas mixture. Therefore, the change represents a measure for these pollutants. For each pollutant, a separate sensor is used, an electrical heating element being assigned to each of which for traversing the temperature range.

SUMMARY

The sensor unit according to the present invention includes two support elements which are combined, in a U shape, in a support unit. The two support elements each form one leg of the U and the slot in between them constitutes a heat barrier. A common support area joins the support elements and supports electrical printed circuit traces and contacts, which make it possible to connect the sensor unit in an electrical receiving socket.

The heat barrier prevents thermal "cross-talk" between the support elements, so that the first heat source cooperates only with the first sensor element, and the second heat source cooperates only with the second sensor element, i.e., the heat barrier creates a thermal isolation between the two sensor elements and between respective sensor element and the heat source not assigned to that sensor element. As a result of the arrangement according to the present invention, the time is shortened that the sensor unit requires, after the heat source(s) is(are) switched on, to reach a stationary temperature distribution and to deliver precise measuring results.

According to a refinement of the present invention, the two support elements form a one-piece support unit. Therefore, the aforementioned "common" support unit does not, as a matter of course, have to be in one piece, but can be composed of two parts, which, however, are secured to each other using appropriate means. Alternatively, it is also possible, discussed above, to combine the two support elements into a one-piece support unit.

In addition, it is advantageous if the support unit is configured as a substrate furnished with electrical printed circuit traces. Consequently, the support unit is preferably constituted by a printed circuit board.

The heat barrier, situated between the two support elements, is to be understood as penetrating the support unit so that at this location something like a thermal air-insulation point is created. It can include a plurality of cutouts arranged in rows, between which lie only thin material segments of the support unit, these thin material segments contributing to the desired thermal isolation. The aforementioned cutout preferably does not extend over the entire longitudinal extent of the support unit, but rather only over a partial segment of the support unit so that the heating elements and the sensor elements lie to the right and to the left of it, and the electrical leads and contacts lie, in the area not occupied by the cutout, in the common support area, in order to be able to plug the sensor unit in an electrical receiving socket.

According to a refinement of the present invention, the two heat sources are configured as electrical resistance leads. The two resistance leads can be configured on the substrate as resistance circuit traces. This results in a very simple design.

It is also advantageous if the two sensor elements are formed by sensor circuit traces arranged on the substrate.

If a printed circuit board furnished with printed circuit traces is used as the substrate, then the substrate is a plate-shaped one, the resistance circuit traces being located on the one side and the sensor circuit traces being located on the other side of the substrate. Consequently, in each case, one resistance circuit trace and one sensor circuit trace are located on the front and back side of the substrate, the heat barrier being located between the two resistance circuit traces and between the two sensor circuit traces, in particular in the form of a slot.

The printed circuit traces may routed up to the edge area of the substrate and, there, form plug-in contacts and/or soldering or welding contacts.

It is also advantageous if the two resistance circuit traces are connected in series, since then the number of plug-in contacts or soldering or welding contacts is very small.

According to a refinement of the present invention, at least one resistance circuit trace is connected in an electrically conductive manner to at least one sensor circuit trace by a via hole (plated-through hole) through the substrate. The via hole is may be electrically connected with only one plug-in contact and/or soldering or welding contact, so that the via hole supplies a common electrical potential, preferably the zero potential, to the electrical heating elements and the two sensor units.

DETAILED DESCRIPTION

Figure 1:
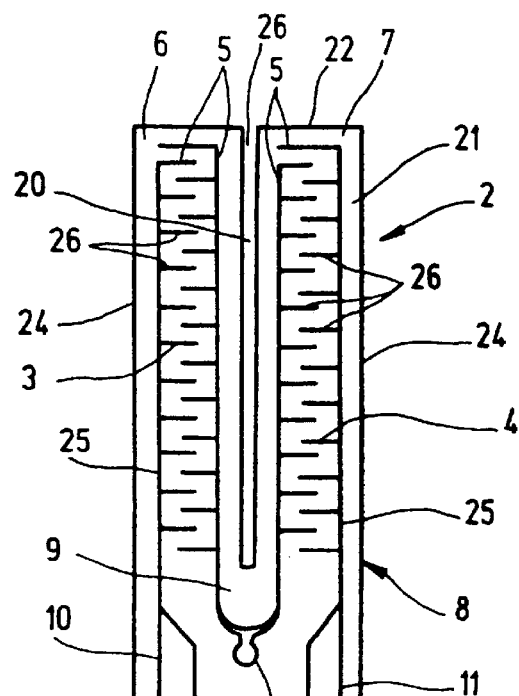
FIG. 1 depicts a front view of measuring or sensor side of a sensor unit according to example embodiment of the present invention.

According to the example embodiment of the present invention is provided a sensor unit 2 for measuring the exhaust gas quality of an internal combustion engine, specifically for determining the nitrogen oxide and carbon monoxide concentration. Sensor unit 2 has a printed circuit board 21, which is bordered by an upper and lower edge 22, 23 and by two side edges 24. On printed circuit board 21, printed circuit traces 25 are applied on both sides. Printed circuit board 21 on its front side has two sensor elements 3, 4. The sensor elements in their longitudinal extent beginning from upper edge 22, occupy roughly three quarters of the length between upper edge 22 and lower edge 23. In the area of lower edge 23 are located the connections of two sensor elements 3, 4. Printed circuit board 21 on its back side has two heating elements 26, 27. During operations heating elements 26, 27, heat sensor elements 3, 4 applied on the front side of printed circuit board 21, in order to be able to carry out the measurement of the exhaust gas quality.

In the following, the structural design of sensor unit 2 is explained in greater detail.

FIG. 1 depicts the front side of printed circuit board 21, the front view of a sensor side 1. In the following, the front side is designated as a sensor side 1. As a result of a central cutout 20 in a partial area of sensor unit 2 arranged in the longitudinal direction of the sensor unit parallel to the side edges, sensor unit 2 has a U-shape. On sensor side 1, a first sensor element 3 and a second sensor element 4 are applied in the form of sensor circuit traces 5. Sensor unit 2 is composed of a first support element 6, opposite which is located a second support element 7, across cutout 20. First support element 6, second support element 7, and a common support area 9 together constitute a support unit 8.

Sensor circuit trace 5 is applied parallel to side edge 24 of first support element 6, from a widened first sensor contact 10 which is located in the area of lower edge 23, up to the area of upper edge 22 of first support element 6. Accordingly, in order to form second sensor element 4, sensor circuit trace 5, in a similar manner, is routed from a widened second sensor contact 11 onto second support element 7.

From sensor circuit trace 5, routed in a straight line in both support elements 6, 7, short segments 26 branch off at right angles in the direction of cutout 20, so that a comb-shaped sensor circuit trace 5 is formed. Similarly comb-shaped sensor circuit traces 5 are situated, in an offset fashion, across from this comb-shaped sensor circuit trace 5, on both support elements 6, 7, so that the segments of exterior sensor circuit trace 5 engage in the gaps between segments 26 of interior sensor circuit traces 5, and vice versa. Between interior sensor circuit traces 5 and exterior sensor circuit traces 5, there exist no electrical connections.

In common support area 9, a via hole 12 is provided, in order to route a common ground from sensor side 1 to heating side 13, located on the back side. Both comb-shaped interior-situated sensor circuit traces 5 are routed to via hole 12.

Figure 2:
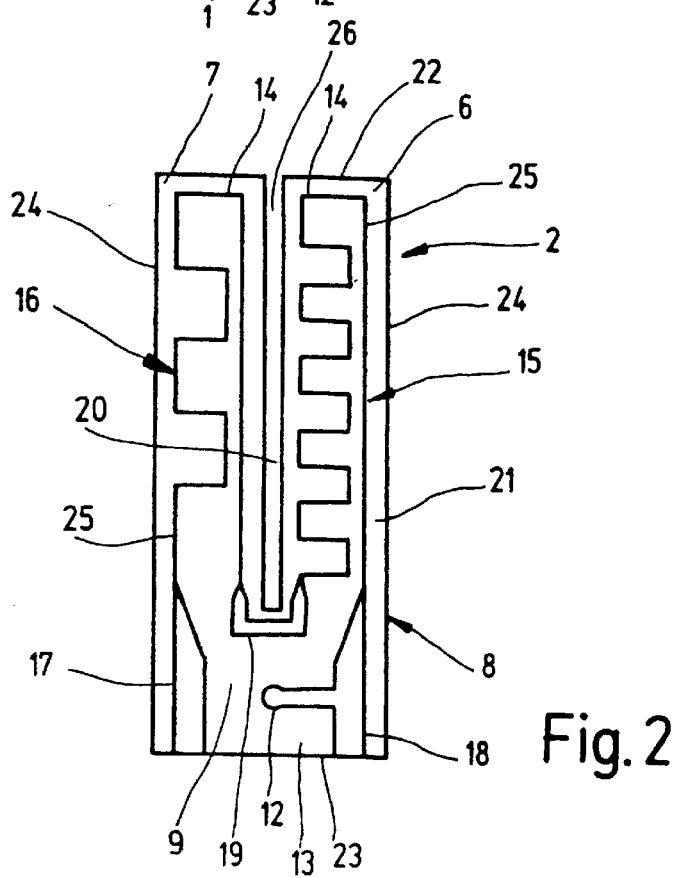
FIG. 2 depicts a rear view of a heating side of the sensor unit.

In FIG. 2, the back side of sensor unit 2 shown in FIG. 1 is depicted. FIG. 2 thus depicts heating side 13. On both support elements 6, 7, a traversing resistance circuit trace 14 is applied. Resistance circuit trace 14 is routed from a widened heating circuit trace contact 17, in the area of lower edge 23, in a meandering fashion on second support element 7, and it runs in a straight line, parallel to side edge 24 of sensor unit 2 back to a widened transition area 19. Resistance circuit trace 14 runs from transition area 19, again in a meandering fashion, on first support element 6, up to upper edge 22, and, from there, runs in a straight line, parallel to side edge 24 of sensor unit 2, back to a widened ground contact 18. The exemplary embodiment, on first support element 6, shows here narrower line loops than on second support element 7. The result is therefore different longitudinal segments of resistance circuit trace 14, and therefore two support elements 6, 7 can be subjected to different temperatures, which are also necessary for the air quality measurement. As a result of this arrangement of resistance circuit trace 14 on two support elements 6 and 7, there results a series circuit of a first heat source 15, of first support element 6, and a second heat source 16, of second support element 7. A widened printed circuit trace leads from ground contact 18, on common support area 9, to via hole 12. In transition area 19 between two heat sources 15, 16, resistance circuit trace 14 is widened in its horizontal extension, in order thus to achieve less electrical resistance than in the area to be heated and therefore to generate less heat radiation.

FIG. 1 and FIG. 2 clearly show, between two support elements 6, 7 in one-piece sensor unit 2, cutout 20 in the form of a straight-line slot 26, in order to obtain greater thermal isolation between the two support elements.

In a further embodiment according to the present invention, not depicted here, both sensor contacts 10, 11 can be configured in a different manner not depicted as in FIG. 1; thus, for example, it is conceivable that widened sensor circuit traces 5 are not routed down to lower edge 23 of support unit 8 and therefore both sensor contacts 10, 11 are also not routed down to lower edge 23 of support unit 8.

A mounting support of sensor unit 2, a contact device, and a measuring and control electronics driving the latter, together with a common housing, are not depicted in FIGS. 1 and 2 for reasons of simplicity.

Mode of Functioning of the Sensor Unit

By applying a heating voltage between heating circuit trace contact 17 and ground contact 18, a heating current flows through resistance circuit trace 14. As a result of the appropriate choice of material, thickness, and routing for the resistance circuit trace, both sensor elements 3, 4, situated on the front side of sensor unit 2, are heated from the current flow, using both heat sources 15, 16. By altering the voltage and thus altering the resulting current, a change in temperature can therefore be effected and thus a characteristic temperature range can be traversed.

By applying two measuring voltages between first and second sensor contact 10, 11 and common ground contact 18 on heating side 13, with the assistance of an undepicted measuring and control electronics and a traversal of a temperature range characteristic for respective sensor units 2, 3, the specific electrical resistance is measured. The characteristic curves determined in this manner (dependence on temperature and electrical resistance), through deviation from a reference curve for unpolluted air, is a measure for the nitrogen oxide and carbon monoxide pollution of the air. Thus a determination of the air quality by measuring two of the chemical compounds relevant, inter alia, for air pollution, nitrogen oxide and carbon monoxide, can be carried out using a one-piece or one-part sensor unit, which is characterized by a simple design and by the material and manufacturing costs associated therewith.

What is claimed is:

1. An air quality sensor, comprising:
   a support unit including two support elements, the support elements forming a U-shape, each of the support elements forming one leg of the U-shape, a slot between the two legs forming a heat barrier, the support unit further including a common support area connecting the support elements to each other and supporting electrical printed circuit traces and contacts for connecting the sensor unit in an electrical receiving socket;
   a respective sensor element arranged on each of the at least two support elements; and a respective heat source assigned to each respective sensor element.

2. The sensor unit according to claim 1, wherein the two support elements form a one-piece support unit.

3. The sensor unit according to claim 1, a wherein the support unit includes a substrate with electrical printed circuit traces.

4. The sensor unit according to claim 3, wherein each respective heat source is configured as an electrical resistance lead.

5. The sensor unit according to 4, claim wherein each resistance lead includes resistance circuit traces on the substrate.

6. The sensor unit according to claim 5, wherein each respective sensor element is formed by sensor circuit traces arranged on the substrate.

7. The sensor unit according to claim 6, wherein the substrate is plate-shaped and the resistance circuit traces are situated on a first side of the substrate, and the sensor circuit traces are situated on a second side of the substrate.

8. The sensor unit according to claim 3, wherein the printed circuit traces are routed to an edge area of the substrate and form at least one of: i) plug-in contacts, ii) soldering contacts, and iii) welding contacts.

9. The sensor unit according to claim 5, wherein the resistance circuit traces are connected in series.

10. The sensor unit according to claim 6, wherein at least one of the sensor circuit traces is connected in an electrically conductive manner to at least one of the sensor circuit traces using a via hole through the substrate.

11. The sensor unit according to claim 10, wherein the via hole is electrically connected to only one plug-in contact, or soldering or welding contact.

* * * * *

UNITED STATES PATENT AND TRADEMARK OFFICE
CERTIFICATE OF CORRECTION

PATENT NO. : 6,314,789 B1 Page 1 of 1
DATED : November 13, 2001
INVENTOR(S) : Peter, Cornelius It is certified that error appears in the above-identified patent and that said Letters Patent is hereby corrected as shown below:

Column 1,
Line 4, change "FIELD OF INVENTION" to -- FIELD OF THE INVENTION --
Line 14, insert -- A sensor of the above-mentioned type is described in European Patent No. 0 527 258 --
Line 28, delete ","

Column 2,
Line 1, change "possible, discussed" to -- possible, as discussed --
Line 18, change "lie," to -- lie --
Line 40, change "may" to -- may be --
Line 55, insert -- BRIEF DESCRIPTION OF THE DRAWINGS --

Column 3,
Line 10, change "operations" to -- operation, --

Signed and Sealed this

Tenth Day of December, 2002

JAMES E. ROGAN
*Director of the United States Patent and Trademark Office*